US006168792B1

(12) United States Patent
Clare-Salzler

(10) Patent No.: US 6,168,792 B1
(45) Date of Patent: *Jan. 2, 2001

(54) MATERIALS AND METHODS FOR DETECTION AND TREATMENT OF IMMUNE SYSTEM DYSFUNCTIONS

(75) Inventor: Michael Clare-Salzler, Gainesville, FL (US)

(73) Assignee: University of Florida, Gainesville, FL (US)

( * ) Notice: Under 35 U.S.C. 154(b), the term of this patent shall be extended for 0 days.

This patent is subject to a terminal disclaimer.

(21) Appl. No.: 08/916,586

(22) Filed: Aug. 22, 1997

Related U.S. Application Data

(63) Continuation-in-part of application No. 08/701,928, filed on Aug. 23, 1996, now Pat. No. 5,939,069.

(51) Int. Cl.$^7$ .......................... A61K 31/18; A61K 31/405; A61K 39/00
(52) U.S. Cl. ................. 424/184.1; 424/85.2; 424/278.1; 424/810; 514/415; 514/605; 514/866; 514/885
(58) Field of Search ..................................... 435/375, 377; 424/85.2, 184.1, 278.1, 810; 514/415, 605, 866, 885

(56) References Cited

U.S. PATENT DOCUMENTS

| | | |
|---|---|---|
| 4,409,243 | 10/1983 | Lieb . |
| 4,490,385 | 12/1984 | Lieb . |
| 5,449,515 * | 9/1995 | Hamilton et al. ..................... 424/85.2 |
| 5,476,659 * | 12/1995 | Goodman et al. ................. 424/278.1 |
| 5,512,447 * | 4/1996 | Baekkeskov et al. ................ 435/7.4 |
| 5,538,854 | 7/1996 | Faustman . |
| 5,601,815 * | 2/1997 | Powrie et al. ....................... 424/85.2 |
| 5,604,260 * | 2/1997 | Guay et al. ........................... 514/605 |
| 5,827,513 * | 10/1998 | Bond et al. .......................... 424/85.2 |

FOREIGN PATENT DOCUMENTS

| | | |
|---|---|---|
| 0436333 | 7/1991 | (EP) . |
| WO 92/20811 * | 11 1992 | (WO) . |
| WO 94/08606 * | 4/1994 | (WO) . |
| 9523599 | 9/1995 | (WO) . |
| 9621654 | 7/1996 | (WO) . |

OTHER PUBLICATIONS

Hellstrand, K. and S. Hermodsson (1989) "Interleukin–2 can induce suppression of human natural killer cell cytotoxicity" Clin. exp. Immunol. 77:410–416.

Faist, E., W. Erthel, T. Cohnert, P. Huber, D. Inthorn, G. Heberer (1990) "Immunoprotective Effects of Cyclooxygenase Inhibition in Patients with Major Surgical Trauma" The Journal of Trauma 30(1):8–17.

Howard et al, Jour. Clin. Immunol., 12, 239–247, 1992.*

*Physicians Desk Reference*, 49th Edition, 1995, pp. 1566–1571.*

Ballif et al, Proc. Natl. Acad. Sci. USA, 93, 5544–5549, 1996.*

Gold et al, Brain, 119, 651–659, 1996.*

Goodwin et al, Clin. Immunol. Immunopathol., 15, 106–122, 1980.*

Mountz et al, Clin. Immunol. Immunopathol., 80, 52–514, 1996.*

Reder et al, Jour. Neuroimmunol., 54, 117–127, 1994.*

Santoli et al, Jour. Clin. Invest., 85, 424–432, 1990.*

Secchi et al, Transplant. Proceed., XVIII, 1540–1542, 1986.*

Trauth et al, Science, 245, 301–305, 1989.*

Wahl, Jour. Clin. Immunol., 12, 61–74, 1992.*

Coffey, R.G., V.A. Alberts, L.L. Weakland (1990) "Prostaglandin–Dependent Desensitization of Human Monocyte cAMP Responses" J Leukocyte Biol. 48:557–564.

Crofford et al. (1994) "Cyclooxygenase–1 and –2 Expression in Rheumatoid Synovial Tissues" J Clin. Invest. 93:1095–1101.

Endres, S. et al. (1991) "Cyclic nucleotides differentially regulate the synthesis of tumor necrosis factor–α and interleukin–1β by human mononuclear cells" Immunology 72:56–60.

Farber, Joshua M. (1992) "A Collection of mRNA Species That Are Inducible in the RAW 264.7 Mouse Macrophage Cell Line by Gamma Interferon and Other Agents" Molecular and Cellular Biology 12(4):1535–1545.

Hafler, David A., Marion Buchsbaum, Howard L. Weiner (1985) "Decreased Autologous Mixed Lymphocyte Reaction in Multiple Sclerosis" Journal of Neuroimmunology 9:339–347.

Howard, M. et al. (1992) "Biological Properties of Interleukin 10" Journal of Clinical Immunology 12(4):239–247.

Kujubu, D.A. et al. (1991) "TIS10, a Phorbol Ester Tumor Promoter–inducible mRNA from Swiss 3T3 Cells, Encodes a Novel Prostaglandin Synthase/Cyclooxygenase Homologue" Journal of Biological Chemistry 266(20):12866–12872.

Mertz, Prema M., David L. DeWitt, William G. Stetler–Stevenson, Larry M. Wahl (1994) "Interleukin 10 Suppression of Monocyte Prostaglandin H Synthase–2" Journal of Biological Chemistry 269(33):21322–21329.

Rasanen, L. et al. (1988) "Defective autologous mixed leukocyte reaction in newly diagnosed type 1 diabetes mellitus" Clin. Exp. Immunol. 71:470–474.

(List continued on next page.)

* cited by examiner

*Primary Examiner*—David Saunders
(74) *Attorney, Agent, or Firm*—Saliwanchik, Lloyd & Saliwanchik

(57) ABSTRACT

The subject invention concerns novel materials and methods for the treatment and/or prevention of autoimmune disease. In a specific embodiment, elevated production of prostaglandin synthase–2 (PGS-2) is correlated with autoimmune dysfunction.

4 Claims, 3 Drawing Sheets

OTHER PUBLICATIONS

Ristimaki, Ari, Susan Garfinkel, Jorg Wessendorf, Thomas Maciag, Timothy Hla (1994) "Induction of Cyclooxygenase–2 by Interleukin–1α" Journal of Biological Chemistry 269(16):11769–11775.

Seldon, Pual M., Peter J. Barnes, Koremu Meja, Mark A. Giembycz (1995) "Suppression of Lipopolysaccharide–Induced Tumor Necrosis Factor–α Generation from Human Peripheral Blood Monocytes by Inhibitors of Phosphodiesterase 4: Interaction with Stimulants of Adenylyl Cyclase" Molecular Pharmacology 48:747–757.

Serreze, David V. (1993) "Autoimmune diabetes results from genetic defects manifest by antigen presenting cells" The FASEB Journal 7:1092–1096.

Spengler, R.N. et al. (1989) "Modulation Of Tumor Necrosis Factor–αGene Expression Desensitization of Prostaglandin $E_2$–Induced Suppression" Journal of Immunology 142(12):4346–4350.

Strassmann, Gideon, Vina Patil–Koota, Fred Finkelman, Miranda Fong, Taku Kambayashi (1994) The Journal of Experimental Medicine 180:2365–2370.

Strieter, R. M. et al. (1990) "Tumor Necrosis Factor–Alpha Gene Expression in Human Whole Blood" Journal of Leukocyte Biology 47:366–370.

Vane, J.R. et al. (1994) "Inducible isoforms of cyclooxygenase and nitric–oxide synthase in inflammation" Proc. Natl. Acad. Sci. USA 91:2046–2050.

Via, Charles S., George C. Tsokos, Bonnie Bermas, Mario Clerici, Gene M. Shearer (1993) "T Cell–Antigen–Presenting Cell Interactions in Human Systemic Lupus Erythematosus" Journal of Immunology 151(7):3914–3922.

Zhong, W.W., P.A. Burke, M.E. Drotar, S.R. Chavali, R.A. Forse (1995) "Effects of prostaglandin $E_2$, cholera toxin and 8–bromo–cyclic AMP on lipopolysaccharide–induced gene expression of cytokines in human macrophages" Immunology 84:446–452.

MATERIALS AND METHODS FOR DETECTION AND TREATMENT OF IMMUNE SYSTEM DYSFUNCTIONS

CROSS-REFERENCE TO A RELATED APPLICATION

This application is a continuation-in-part of application Ser. No. 08/701,928 filed On Aug. 23, 1996, now U.S. Pat. No. 5,939,069.

BACKGROUND OF THE INVENTION

Diabetes is a term that refers to a collection of diseases resulting in disordered energy metabolism and varying degrees of blood glucose elevations or hyperglycemia. One of the best characterized forms of the disease is that which arises from an immunologically mediated destruction of the insulin secreting pancreatic beta cells. This severe form of the disease is termed Insulin-dependent Diabetes (IDD or IMD) since it is associated with progressive insulin deficiency and coincident symptoms such as weight loss, glycosuria and polyuria, and increased thirst or polydipsia. Other terms for this form of diabetes are Type 1 Diabetes (cf. Type 2 Diabetes which results from an inherent resistance to insulin action); Ketosis Prone Diabetes because there is abnormal generation of ketone bodies as a result of excessive breakdown of body fats due to the severe insulin deficiency; or Juvenile Diabetes, since virtually all diabetes that appears in childhood and adolescence is of this type.

Diabetes is a major public health problem, especially in Western countries. The incidence rates vary greatly worldwide, from as high as 40 per 100,000 persons in Finland to as low as 1–2 per 100,000 among the Japanese. The peak incidence is during the pubertal years, associated with the increasing bodily demands for insulin associated with muscle growth. The prevalence rates in the United States population under age 20 years is 0.25% and it approaches 0.4% over a lifetime, albeit an estimated 10–20% of patients with Non Insulin-dependent Diabetes (NIDD) or Type 2 or Maturity Onset Diabetes also have, in reality, slowly progressive IDD. Thus, it is estimated that there may be at least 1 million Americans affected by IDD.

Diabetes results in progressive damage to the blood vessels of the body, to a degree that depends upon the severity of hyperglycemia and its duration. The incident mortality rate for IDD has been calculated to be 7-fold higher than for age matched non-diabetic controls. Whereas the decade long Diabetes Control and Complications Trial (DCCT)—concluded in 1994 by the National Institutes of Health in the United States—showed that meticulous insulin replacement therapy would slow the appearance of damaged arteries, it was not able to completely prevent this damage since blood glucose levels were difficult to keep within normal limits. Ocular complications of diabetes are the leading cause of new blindness in persons 20–74 years of age. The risk of lower extremity amputation is 15-fold higher in those with diabetes. Approximately 40% of persons undergoing renal transplantations have kidney failure because of diabetes, and the proportion due to diabetes continues to rise each year. Women with diabetes produce newborn infants with a 7% newborn mortality rate. Other complications of diabetes include increased heart disease and stroke, loss of nerve cells or neurons enervating the limbs and intestine, impotence and infertility, cataract formation in the lens of the eyes, increased periodontal disease, and predisposition to infectious diseases especially from bacteria and yeast Of all patients with diabetes, those with IDD have a disproportionate share of these complications because of its severity and usual early age of onset. In the United States, the direct health care costs attributable to diabetes in 1994 have been estimated to exceed $120 billion. Thus it is important that the pathogenesis of IDD be understood and strategies be developed to prevent it as a fully expressed clinical disease.

Patients with IDD are unusually prone to other diseases that have become recognized as having autoimmune origins. These diseases include thyroiditis or Hashimoto's disease, Graves' disease, Addison's disease, atrophic gastritis and pernicious anemia, celiac disease, and vitiligo (Maclaren, N. K. [1985] *Diabetes Care* 8(suppl.):34–38). Evidence that IDD itself has an autoimmune nature began with histological studies of patients; these studies indicated that the islets were infiltrated with a chronic inflammatory (lymphocytic) infiltrate termed insulitis. This was supported in the early 1970s by reports of islet cell autoantibodies reactive to antigens within the cytoplasm (ICA) (Lendrum et al. [1975] *Lancet* 1:880–882) or confined to the islet cell surfaces (ICSA) (Maclaren et al. [1975] *Lancet* 1:977–1000) as detectable by indirect immunofluorescence. Later it was recognized that many patients also develop autoantibodies to insulin (IAA) before their diagnosis (Palmer et al. [1983] *Science* 222:1337–1339) as well as to insulin receptors (Maron et al. [1983] *Nature* 303:817–818). Autoantibodies were also reported to an islet cell protein composition of 64,000 M. Wt. in man (Baekkeskov et al. [1982] *Nature* 298:167–169), in the Biobreeding (BB) rat model (Baekkeskov et al. [1984] *Science* 224:1348–1350), and in the Non Obese Diabetic (NOD) mouse model (Atkinson and Maclaren [1988] *Diabetes* 37:1587–1590). 64 kDa antigen has subsequently been reported to be the lower molecular weight isoform of glutamic acid decarboxylase ($GAD_{65}$) (Baekkeskov et al. [1990] *Nature* 347:151–156) (Kauffman et al. [1992] *J. Clin. Invest.* 283–292). GAD is an enzyme that converts glutamate into the membrane stabilizing neurotransmitter called gamma amino butyric acid or GABA. In addition to autoantibodies to GAD, peripheral blood mononuclear cells were shown to be autoreactive in patients developing IDD (Atkinson and Maclaren et al. [1992] *Lancet* 339:458–459; and Harrison et al. [1993] *Lancet* 341:1365–1369).

It has previously been demonstrated in several autoimmune diseases, including IDD, systemic lupus erythematosus (SLE), rheumatoid arthritis (RA), multiple sclerosis (MS), and autoimmune thyroid disease,:that antigen-presenting cells (APCs) such as monocytes and macrophages are dysfunctional in their ability to activate T lymphocytes (Via, C. S. et al. [1993] *J. Immunol.* 151 :3914–3922; Serreze, D. [1993] *FASEB J.* 7:1092–1096; Rasanen, L. et al. [1988] *Clin. Exp. Immunol.* 71:470–474; Hafler, D. A., et al. [1985] *J. Neuroimmunol.* 9:339–347). The defect(s) in APC function, however, have thus far not been defined at the cellular or molecular level.

Prostaglandins (PGs) are lipid molecules formed from a precursor molecule, arachidonic acid, through the actions of specific enzymes called prostaglandin synthases (PGS-1 and PGS-2). PGS-1 mRNA and protein are constitutively expressed, and this enzyme is responsible for the production of low levels of PGs and functions as a housekeeping molecule. PGS-2 is an inducible enzyme expressed by macrophages and monocytes during inflammation and following exposure to mitogens, cytokines, and bacterial cell wall products, i.e., lipopolysaccharide (LPS) (Farber, J. M. [1992] *Mol. Cell. Biol.* 12:1535–1545; Vane, J. R. [1994] *Proc. Natl. Acad. Sci. USA* 91:2046–2050; Kujubn, D. A.

[1993] *J. Biol. Chem.* 266:12866–12872; Ristimaki, A. et al. [1994] *J. Biol. Chem.* 269:11769–11775). PGS-2 has been shown to be expressed in the cells lining the joints of individuals with rheumatoid arthritis and may contribute to the ongoing inflammation in the affected joint (Crofford, L. J. et al. [1994] *J. Clin. Invest.* 93:1095–1101).

In addition to prostanoids, monocytes produce monokines that strongly modify inflammation and immune responses. Among the monokines that in general upregulate or promote inflammation and immunity are TNFα, IL-1α, IL-1β, IL-12, and IL-6. Monokines that tend to downregulate these responses are IL-4, IL-10, IL-13, and IL-1 receptor antagonist (IL-1RA).

Prostaglandins are known to have an effect on the expression of monokines. For instance, prostaglandin $E_2$ ($PGE_2$) is known to suppress the production of TNFα (Seldon, P. M. et al. [1995] *Mol. Pharmacol.* 48:747–757; Strieter, R. M. et al. [1990] *J. Leuk. Biol.* 47:366–370). There are also reports that $PGE_2$ suppresses IL-1α (Endres, S. et al. [1991] *Immunology* 72:56–60; Zhong, W. W. [1995] *Immunology* 84:446–452). In contrast to its suppressive effects, $PGE_2$ production stimulates the production of IL-10 by monocytes (Strassman, G. et al. [1994] *J. Exp. Med.* 180:2365–2370). IL-10 in turn modulates $PGE_2$ production by suppressing PGS-2 production (Mertz, P. M. et al. [1994] *J. Biol. Chem.* 269:21322–21329). In addition, IL-10 stimulates the production of another potent immunoregulatory monokine, IL-1RA (Spengler, R. N. et al. [1989] *J. Immunol.* 142:4346–4350). $PGE_2$ therefore can stimulate immunoregulation through its own action and through its actions on monokine production.

If monocytes are chronically exposed to $PGE_2$ in vitro, there is a loss of response to its action. This desensitization phenomena is mediated by the down-regulation of $PGE_2$ receptors (Coffey, R. G. et al. [1990] *J. Leuk. Biol.* 48:557–564). For example, $PGE_2$ in vitro normally suppresses TNFα production, but chronic exposure leads to a loss of suppression of this monokine by $PGE_2$. Removal of, or blocking, $PGE_2$ can reverse the desensitization process (Howard, M. et al. [1992] *J. Clin. Immunol.* 12:61–784).

Currently, one can screen for individuals at high risk for the development of IDD by serologic methods only, which reflect autoimmune B and T lymphocyte activity. Serologic tests identify approximately 80–85% of individuals who have existing autoimmune disease against the insulin-producing cells of the pancreas. Of the ICA+ population, approximately 80–85% will develop IDD within the ensuing five years. Currently no test exists, immunologic, genetic, or otherwise, which can identify individuals at risk for IDD other than these serologic tests.

Because IDD takes several years to develop in an individual, autoimmunity may be firmly established at the time that individuals develop ICAs. Detection of background cellular or genetic factors necessary for the development of autoimmune disease and expressed early in the disease process is of great clinical importance. Detection of these factors would preferably identify individuals before autoimmunity is initiated, or perhaps at earlier stages of the disease than detected by ICA. Earlier detection would be of great clinical importance in identifying individuals at high risk for disease where the administration of preventative therapies that attempt to preserve the residual insulin-secreting cells are employed.

BRIEF SUMMARY OF THE INVENTION

The subject invention pertains to materials and methods for the detection, prevention, and treatment of diabetes, other autoimmune conditions, and conditions involving dysfunctional apoptotic processes. In a specific embodiment, the subject invention concerns the identification of a deject in antigen-presenting cells (APCs) that is associated with diabetes and other autoimmune disorders. One aspect of this defect is the elevated production of prostaglandin synthase-2 (PGS-2) in cells of individuals who have developed or will develop autoimmune disease.

In a specific embodiment of the subject invention, diabetes and/or other autoimmune disease can be predicted and/or monitored by assaying for expression of prostaglandin synthase-2 (PGS-2) by antigen-presenting cells. Thus, one aspect of the invention is the discovery that PGS-2 is a cellular marker that is strongly associated with clinical autoimmune diseases such as IDD. In a preferred embodiment, the antigen-presenting cells which are monitored for diagnostic purposes are macrophages and/or monocytes. Expression of PGS-2 in these cells is an indicator of autoimmune susceptibility or disease.

The expression of PGS-2 can be detected in any of a number of ways which would be apparent to those skilled in the art having the benefit of this disclosure. For example, the expression of PGS-2 can be detected by the presence of PGS-2 messenger RNA (mRNA), presence of the PGS-2 protein itself, or by detecting biological effects of the PGS-2 protein, i.e., $PGE_2$ production.

A further aspect of the subject invention pertains to the identification of diagnostic markers for autoimmune disease on T cells. In one embodiment it has been found that CD25 expression on T-cells can be correlated with autoimmune disease such as IDD. Specifically, it has been found that individuals with a susceptibility to diabetes have a lower level of expression of CD25 on T-cells. Furthermore, inhibition of $PGE_2$ was found to significantly increase CD25 expression in cells of individuals at risk for IDD. Inhibition of $PGE_2$ did not enhance expression of CD25 in individuals who are not at risk to develop IDD. In a further embodiment, individuals at risk for IDD have been found to have decreased levels of FAS receptor expression compared to individuals who are not at risk to develop IDD. In a preferred embodiment T-cells which express both FAS receptor and CD25 are examined for a reduced level of expression of these proteins. A reduced, level of expression of FAS receptor and CD25 compared to normal controls is indicative of diabetes or other autoimmune conditions.

Assays for PGS-2 expression, CD25 expression and/or FAS receptor expression add new dimensions to disease prediction such as assessing disease activity and progression, and predisposition for developing other autoimmune diseases.

The diagnostic procedures described herein can be used to detect evidence of autoimmune dysfunction before the appearance of clinical symptoms. This early detection makes it possible to initiate appropriate preventative measures.

A further aspect of the subject invention is the discovery that pharmacologic inhibition of PGS-2 has potent inhibitory effects on the development of autoimmune disease.

In one embodiment, prevention of IDD can be achieved according to the subject invention by drug therapy that blocks PGS-2 enzymatic activity. PGS-2 inhibitors provide an inexpensive, safe, and well-tolerated approach to the prevention of this disease. Furthermore, the efficacy of therapy can be monitored by measuring serum or urine $PGE_2$ levels. Also, for certain individuals, PGS-2-specific inhibitors were found to markedly reduce production of PGE$_2$ and increase IL-1 receptor antagonist (IL-1RA) in human monocytes.

A further aspect of the subject invention pertains to treatments for diabetes or other autoimmune disease which comprise modulating CD25 expression and/or FAS receptor expression. In a preferred embodiment, individuals at risk for IDD are treated to increase CD25 expression. This increase can be effected by, for example, administering a compound which inhibits PGS-2 activity, PGE2 activity, or the activity of cyclic AMP or related compounds. Such inhibition can be achieved by, for example, an inhibitor of PGS-1 or PGS-2. In a preferred embodiment, a PGS-2 specific inhibitor such as NS398 is administered.

A further aspect of the subject invention pertains to diagnostic and therapeutic methods based on modulation and/or detection of cell death mechanisms and events. In accordance with the subject invention, differences in cell death events relating to expression or activity of PGS-2 and/or related molecules can be exploited to provide critical diagnostic information or to intervene in disease processes. In a specific embodiment, individuals at risk for cancer or to develop autoimmune diseases will display a PGS-2 related resistance to cell death upon stimulation of cells by chemical factors including, but not limited to, TNFα and FAS ligand. By intervening in this process by, for example, the administration of inhibitors of PGS-2-related activity, it is possible to facilitate the completion of cell death events to eliminate inappropriate cells from the biological milieu. In this way, autoimmune T-cells can be removed through the apoptic mechanism upon stimulation by appropriate chemical signals or imunnization with disease-related target antigens such as insulin or GAD. Similarly, cancer cells can also proceed to appropriate cell death, thereby preventing or reducing tumors and/or other inappropriate cellular proliferation.

Thus, a further specific embodiment of the subject invention concerns the administration of inhibitors of PGS-2, or its biological activities, to effect a modulation of programmed cell death such that self-destructive T-cells and/or cancer cells are removed to reduce or prevent autoimmune or cancer conditions. The inhibitors of PGS-2 which can be used according to the subject invention include, but are not limited to, glucocorticoid hormones (which suppress expression of PGS-2), IL-10, IL4, IL-13, and TGF-β.

In a further embodiment of the subject invention modulation of cell death can be achieved by upregulating the cellular response resulting from activation of the FAS receptor. This upregulation can be achieved by administration of an agent which increases FAS receptor expression. This agent may be, for example, a PGE inhibitor. Alternatively, the upregulation of the FAS cellular response can be achieved by, for example, administration of agents which enhance the intracellular response to FAS receptor activation. Thus, in individuals having a pathological condition attributable to aberrant cell death processes, cell death can be promoted by upregulating the intracellular cascade of events whereby FAS receptor activation ultimately promotes cell death. This upregulation can be achieved by those skilled in the art, having benefit of the instant disclosure, by, for example, stimulating enzymatic and other regulatory molecules which participate in the FAS activation pathway. In a specific embodiment, individuals identified as needing increased T-cell death can be treated to increase both CD25 expression and cellular response to FAS receptor activation. This therapy can be further augmented by administration of an appropriate antigen thereby enhancing CD25 activation and increasing the specificity of the treatment. The antigen may be, for example, an autoantigen.

DETAILED DISCLOSURE OF THE INVENTION

Figure 1:
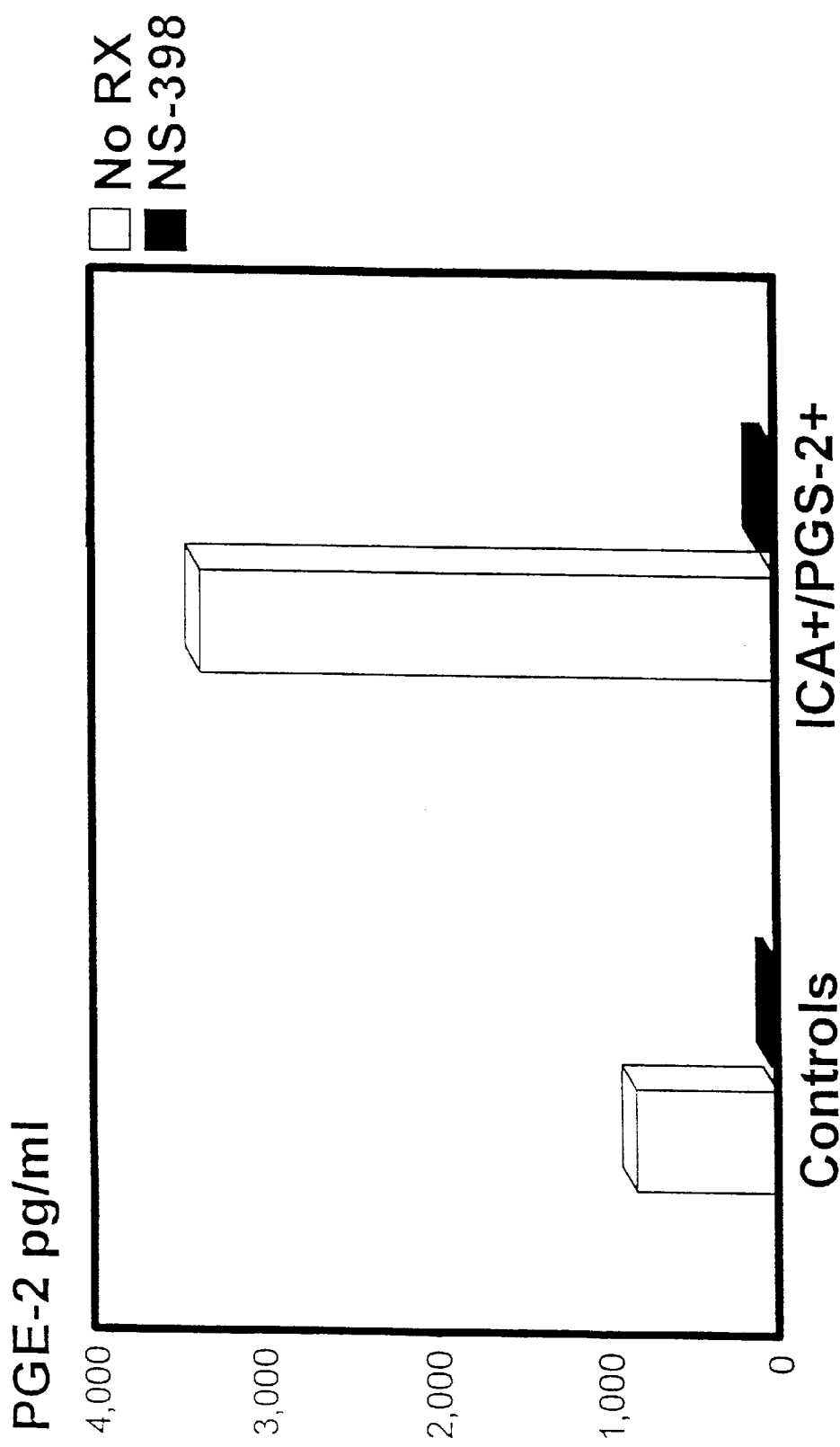
FIG. 1 shows the blocking of PGE$_2$ production by the PGS-2-specific inhibitor, NS-398.
Figure 2:
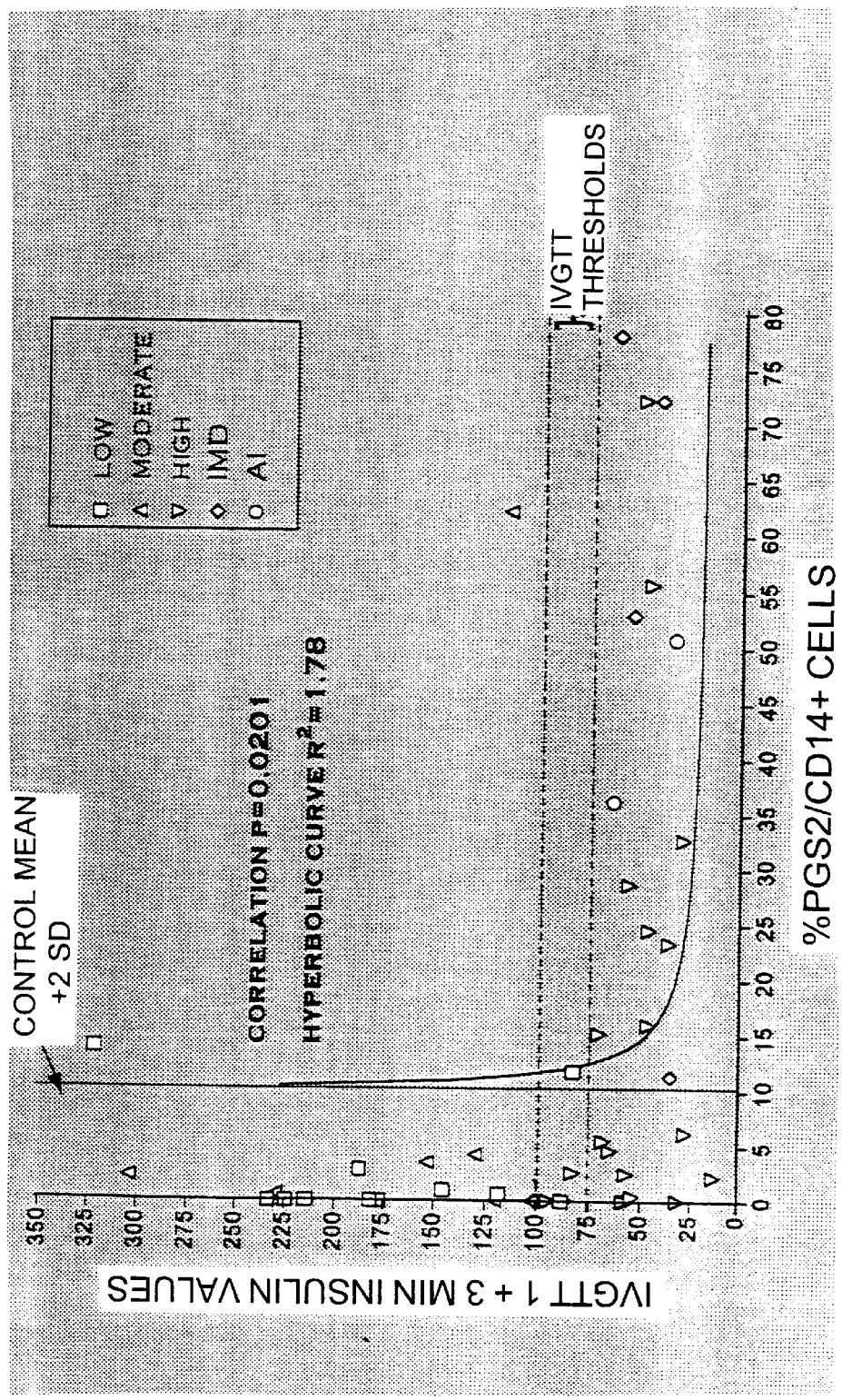
FIG. 2 shows the correlation between increased PGS-2 levels and an increased risk of IDD.
Figure 3:
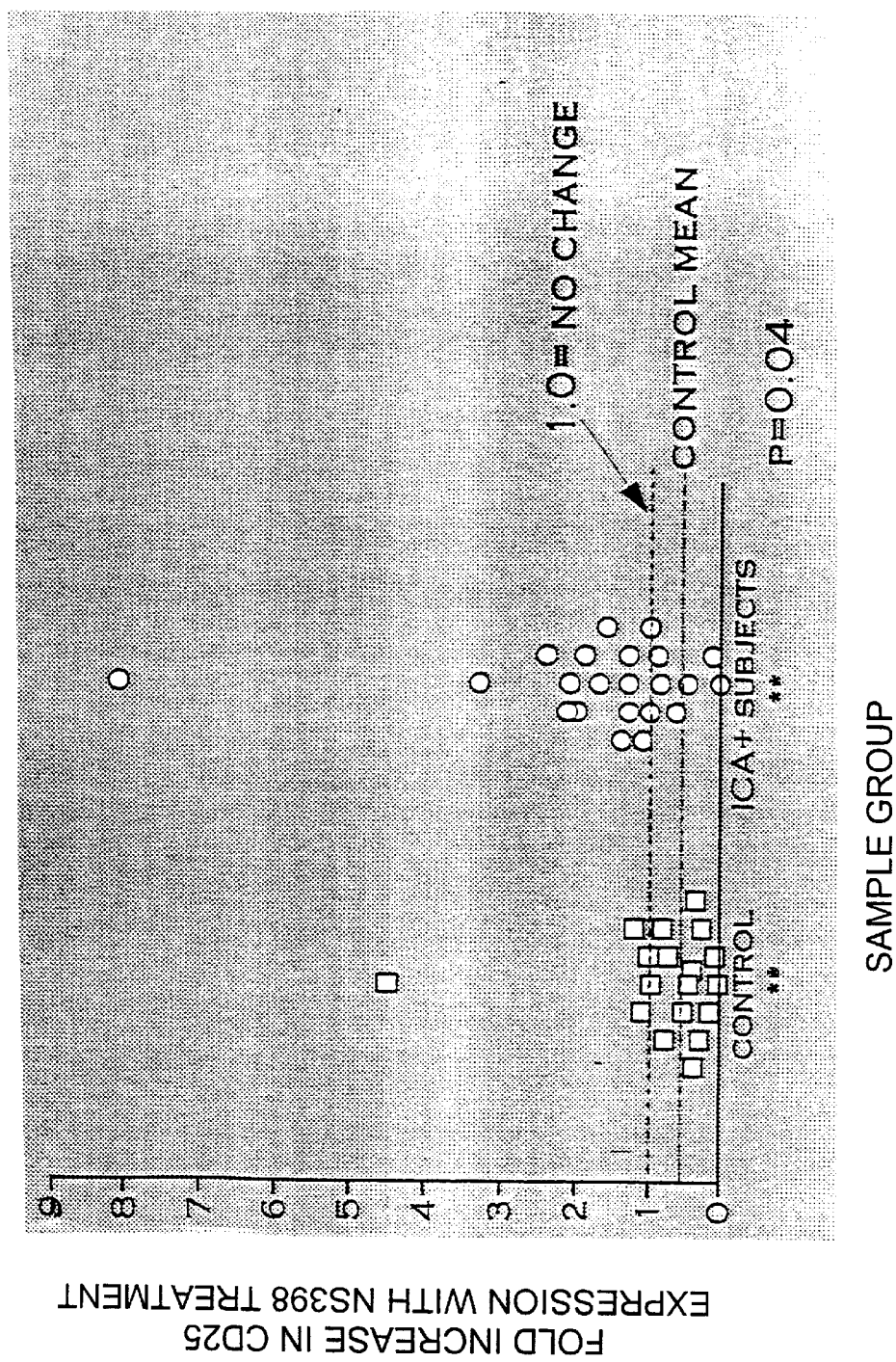
FIG. 3 shows the ability of a PGS-2 inhibitor to increase expression of CD25.

In one aspect the subject invention pertains to the detection and/or modulation of prostaglandin synthase-2 (PGS-2) production in antigen-presenting cells (APCs) of individuals at risk for developing autoimmune disease or cancer. In this embodiment, the subject invention concerns the discovery that PGS-2 is a cellular marker for individuals at risk for IDD and other autoimmune diseases. Another embodiment of the subject invention concerns preventative or therapeutic treatments. In a preferred embodiment, drugs that block PGS-2 production or activity can be administered to individuals who have autoimmune disease or cellular proliferation disease, or are at risk for developing such diseases. In a further embodiment, the subject invention pertains to monitoring and/or modulation of CD25 expression and/or FAS receptor activation of T-cells or other cells having dysfunctional cell death processes.

The subject invention provides quick and easy procedures for determining whether an individual may be at risk for developing autoimmune disease. In one diagnostic aspect of the invention, peripheral blood monocytes can be evaluated to determine the level of PGS-2 expression. This evaluation can be conducted using any one of a number of diagnostic procedures well known to those skilled in the art. These procedures may be used to detect PGS-2 directly or to detect evidence of PGS-2 expression. Evidence of PGS-2 expression includes, for example, the presence of PGS-2 mRNA. The PGS-2 mRNA can be detected by, for example, reverse transcriptase PCR (RT-PCR). PGE$_2$, which is produced on account of the enzymatic activity of PGS-2, can readily be detected using, for example, ELISA, RIA, or other antibody-based assays. The expression of PGS-2 protein can also be detected using flow cytometry methods or Western blotting.

In a further diagnostic aspect of the subject invention, T-cells are evaluated to determine levels of CD25 expression and/or FAS receptor expression. A decrease in expression of either CD25 or FAS receptor has been found to be indicative of risk for autoimmune disease-particularly IDD. A decrease in the combined expression of CD25 and FAS receptor is particularly indicative of risk for autoimmune disease. The level of expression of these molecules can be readily ascertained by those skilled in the art using standard techniques such as, for example, FACS analysis using commercially available antibodies. A further diagnostic procedure involves the determination of the increase in CD25 expression resulting from the administration of a PGE-2 inhibitor. An increase in CD25 expression on T-cells upon treatment with a PGE-2 inhibitor is indicative of risk for autoimmune disease including IDD. The PGE-2 inhibitor may be, for example, NS398 or indomethacin, which inhibits both PGS-1 and PGS-2.

The diagnostic assays of the subject invention can be used to detect evidence of autoimmune disease before the appearance of clinical systems. Furthermore, the assays are useful for monitoring disease progression or the effect of treatment.

In a therapeutic and/or preventative aspect of the subject invention, the action of prostaglandins can be blocked or inhibited, thereby slowing or eliminating undesirable immune processes. In a preferred embodiment, the activity of PGS-2 and/or related molecules can be blocked. Indomethacin is known to block the activity of PGS-2. Aminoguanidine is an inhibitor of inducible nitric oxide synthase (iNOS). NO augments PGS-2 activity. Thus, the subject invention provides a method for reducing the severity of autoimmune disease. As used herein reference to "reducing the severity" of a disorder would include preventing or delaying the disorder or making the effects of the disorder less damaging physically or emotionally.

Treatment of NOD mice afflicted with active, established autoimmune disease using a drug combination of indomethacin and aminoguanidine markedly delays the onset and reduces the incidence of diabetes. The combination of inhibitors is particularly effective. Furthermore, treatment of NOD mice at an early stage of disease with indomethacin alone effectively blocks the development of IDD. It has also been found that the PGS-2-specific inhibitor, NS-398 (available from Cayman Chemical Company), effectively blocks all PGS-2 production in vitro from monocytes of individuals at high risk for IDD. Treatment of individuals at high risk for IDD can be used to block the progression of autoimmunity to frank diabetes.

The treatments of the subject invention are also useful to reduce the severity of the side effects of autoimmune disease. In a particularly preferred embodiment the side effects of diabetes can be reduced by treatment with a prostaglandin inhibitor.

In a further embodiment of the subject invention, PGS-2-specific inhibitors can be used in conjunction with antigen-specific immunization therapy. In the immunization treatment paradigms, a target antigen for IDD, or other autoimmune disease, is used to immunize the individual This results in tolerance and a lack of progression to overt disease. In the case of diabetes, antigens useful in this regard include, but are not limited to, insulin, GAD, IA-2, IA-2β, and fragments and variants of these antigens. Antigens associated with various autoimmune conditions include, but are not limited to, those shown below in Table 1.

TABLE 1

| Condition | Antigens |
| --- | --- |
| Multiple Sclerosis | myelin basic protein |
|  | proteolipid protein |
| Rheumatoid Arthritis | collagen |
| Lupus | DNA |
|  | histone proteins |
| IDDM | GAD |
|  | insulin |
|  | IA-2 |
|  | IA-2β |
|  | 38 kD protein |
|  | perforin |
| Thyroid | thyroglobulin |
|  | peroxidase |
| Vitiligo | tyrosinase |

As PGs inhibit lymphocyte activation, and activation is a prerequisite for apoptosis of T cells, treatment of subjects with PGS-2 inhibitors prior to, or concurrent with, immunization can potentiate the effects of this therapy. Therefore, PGS-2 inhibitors can be used as an adjuvant therapy for antigen immunization to prevent IDD or other autoimmune diseases.

The monocyte production of the monokines IL-1β, TNFα, IL-1RA, and IL-10 in culture supernatants from healthy controls and the pre-diabetic population in the presence and absence of the PGS-2-specific inhibitor, NS-398, have been evaluated. It has been determined that NS-398 promotes the production of the immunoregulatory monokines IL-10 and IL-1RA, suggesting that high levels of PGE2 produced by pre-diabetic monocytes result in $PGE_2$ desensitization. It has also been determined that, despite enhanced levels of PGS-2 and $PGE_2$ in diabetic and pre-diabetic individuals, there is no corresponding increase in IL-10. Furthermore, in NOD mice, administration of IL-10 surprisingly does not inhibit $PGE_2$ production by monocytes. Therefore, a further aspect of the subject invention is a method for detecting evidence of autoimmune disease, particularly diabetes, which comprises evaluating monocytes to determine if those monocytes have a reduced response to IL- 10 with regard to PGS-2 expression. Such reduced response would be evidence of disease. In accordance with these findings, compounds that inhibit prostaglandin production can be used to modulate the production of anti-inflammatory monokines in order to limit the immune response. The spontaneous expression of PGS-2 and the production of PGE by pre-diabetic monocytes may influence their function, limiting their ability to produce monokines that would have a potent effect on limiting the autoimmune response to the β-cells of the islet and therefore would promote the progression to diabetes.

Treatments that inhibit $PGE_2$ can be used according to the subject invention to restore the production of these potent regulatory monokines and either slow or block the autoimmune process, as well as to promote appropriate apoptotic processes. In addition, the production of IL-10 by the monocyte can be used to promote the production of Th2 lymphocytes that are thought to play an important regulatory role in IDD. Furthermore, blocking $PGE_2$ and limiting prostaglandin desensitization can also be used to promote the generation of TH2 cells as $PGE_2$ promotes the generation of these cells.

A further therapeutic embodiment of the subject invention pertains to the modulation of CD25 expression of T-cells. In a related aspect of the subject invention the cellular response to FAS receptor activation can be modulated. For individuals at risk for IDD or in need of increased programmed cell death, the subject invention provides a treatment whereby the efficiency of the cell death pathway is enhanced. This enhancement is accomplished by increasing expression of CD25 and/or the response to FAS receptor activation. In a preferred embodiment, the enhancement of CD25 expression can be accomplished by administering an inhibitor of $PGE_2$. Upregulation of FAS-related cellular activation is preferably achieved by increasing expression of the FAS protein or by enhancing the amount, or activity, of compounds which promote the intracellular FAS activation pathway. In one embodiment, this therapy is augmented by the administration of an antigen thereby enhancing the activity resulting from expression of CD25. The antigen may be, for example, an autoantigen.

In a specific embodiment, the subject invention comprises administering a prostaglandin inhibitor to an individual who has been determined to be at risk for developing autoimmune disease. In a preferred embodiment, the prostaglandin inhibitor is administered chronically. In a further preferred embodiment, the prostaglandin inhibitor is administered at a dose which is higher than that which would be used, for example, to relieve pain or inflamation. In this regard, the inhibitor should be administered at a dosage and in a manner which will effectively increase expression of CD25 on T-cells. In a particularly preferred embodiment, the prostaglandin inhibitor is an inhibitor of PGS-2. The therapy of the subject invention is particularly advantageous when administered prior to the appearance of clinical symptoms of autoimmune disease or the need for enhanced programmed cell death.

Materials and Methods

RT-PCR detection of PGS-2 mRNA in human monocytes. Human peripheral blood is collected in sterile green top 10 ml tubes. Assays are preferably performed with 5 ml or more of blood. The blood is then centrifuged on a ficoll gradient for 30 minutes at 1500 rpm. Monocytes are isolated to >80% purity by adherence for 2 hours to a plastic culture surface. Cells are then cultured overnight in RMPI-1640 plus endotoxin-free fetal calf sera. The cells are harvested after 16 hours of culture by cold $Ca^{++}/Mg^{++}$-free PBS, the cells are counted, and viability is assessed. Monocytes cultured in 10 µg/ml LPS serve as a positive control for each sample tested. The poly mRNA is then harvested from a standard $10^5$ monocytes using a kit (Quiagen). The mRNA is then reverse transcribed in a standard reaction mixture. The cDNA is then amplified by PGS-2-specific primers designed by our laboratory using a standard reverse transcriptase reaction for 45 cycles. The PCR product is then run out on agarose gels with known standards and the size confirmed. β-actin is used as an internal control in these reactions. The identity of RT-PCR products were confirmed by size and Southern blotting using a PGS-2-specific labeled internal probe.

PGS-2 protein detection in human monocytes. A PGS-2-specific mouse monoclonal antibody (Cayman Chemical Company) has been utilized for detection of PGS-2 protein in monocytes. Cells for immunocytochemistry are adhered to multichamber slides for two hours, fixed in 0.2% paraformaldehyde, and permeabilized with Triton-X and glycine in PBS for 10 minutes. The primary antibody is incubated overnight at 4° C. and then detected with FITC labeled Fab goat anti-rabbit antisera. The cells are then visualized with a fluorescent microscope.

A fluorescent activated cell sorting (FACs) method can also be used for detection of PGS-2 in monocytes. In this procedure, whole blood is labeled with an anti-monocyte antibody CD14 coupled to a phycoerythrin molecule. The cells are then fixed and lysed with FACs-Lyse (Becton-Dickenson). The cells are then further permeabilized with saponins throughout the procedure, and then analyzed on a FACs machine. The percent of monocytes positive for PGS-2, as well as fluorescent intensity, is then determined. Approximately 15%–70% of peripheral blood monocytes from ICA+ individuals are positive by this method.

Following are examples which illustrate procedures for practicing the invention. These examples should not be construed as limiting. All percentages are by weight and all solvent mixture proportions are by volume unless otherwise noted.

Example 1—Detection of PGS-2 mRNA

The regulation of mRNA and protein expression of PGS-2, the inducible enzyme critical for the production of large quantities of prostaglandins, was examined in macrophages of the NOD mouse. Macrophages from control mouse strains did not express PGS-2 mRNA as determined by the highly sensitive reverse transcriptase polymerase chain reaction. The PGS-2 protein is likewise not expressed in resting control macrophages as assessed by indirect immunofluorescence using a PGS-2 specific antibody. In marked contrast, NOD macrophages spontaneously express high levels of mRNA and protein for this enzyme as determined by these techniques. PGS-2 was also found to be expressed in the macrophages of NODscid/scid mice which lack functional T and B cells and, as a result, do not develop autoimmune disease or diabetes. The expression of PGS-2 in macrophages of NODscid/scid mice indicates that spontaneous PGS-2 expression is not dependent on the autoimmune milieu, and suggests that PGS-2 expression is a result of a primary macrophage defect. Therefore, the aberrant expression of PGS-2 by NOD macrophages readily explains the abnormal PG production by these cells and provides the molecular and cellular basis for APC dysfunction.

Example 2—Role of PGS-2 Expression in IDD

In order to more fully establish the genetic contribution of PGS-2 expression to autoimmunity in the NOD mouse, congenic mice were examined. The gene encoding PGS-2 is located on chromosome 1, 76.2 CM from the centromere. These mice, designated B6.NOD.C1, have a segment of chromosome 1 from the NOD mouse that contains the "NOD PGS-2 gene," while the rest of the mouse genome is from the non-autoimmune C57BL/6 mouse. Macrophages from B6.BOD.C1 congenic mice, like the NOD, spontaneously express PGS-2 mRNA and protein. These mice develop autoimmune disease in the pancreas, but unlike the NOD, do not develop diabetes. The absence of diabetes in these congenic mice is likely due to a lack of other key genes from the NOD that contribute other important factors to the overall disease process. Another line of congenic mice were designated NOD.B10.C1. These mice contain the NOD genome except for a segment of chromosome 1 derived from the non-autoimmune C57BL/10 mouse and contains the "C57BL/10 PGS-2 gene." NOD.B10.C1 mice do not spontaneously express PGS-2 and have a 40–50% reduction in the incidence of diabetes. These data, along with those from the B6.NOD.C1 congenic mice suggest that the expression of PGS-2 correlates with a more aggressive autoimmune phenotype.

Example 3—Blocking Activity of PGS-2 as Therapy for IDD

Blocking the activity of PGS-2 with drugs that reduce PG production can be used to prevent or slow the development of IDD disease. When NOD mice with established, active autoimmune disease are treated through their drinking water with a combination of drugs, including a PGS-1/PGS-2 inhibitor, low dose indomethacin (3 µg/ml), in conjunction with an inducible nitric oxide synthase (iNOS) inhibitor, aminoguanidine, which potentiates the effects of indomethacin, the incidence of diabetes in NOD mice drops by 42% in comparison to control animals and animals treated with either low dose indomethacin or aminoguanidine alone.

Treatment of NOD mice at a time when autoimmunity is in its final stages with high doses (15 µg/ml) of indomethacin alone reduces the incidence of diabetes from 77% to 22%. These data demonstrate a strong effect of PGS inhibitors on the development of IDD.

Example 4—Association of PGS-2 and PGE with Autoimmune Disease

The effects of non-steroidal anti-inflammatory drugs (NSAIDs) that specifically inhibit PGS-2 in vitro were assessed, and they were found to be highly potent blockers of NOD mouse macrophage PGS-2 production. Aspirin-like drugs that inhibit both PGS-1 and PGS-2 cause gastric irritation, whereas PGS-2-specific drugs do not.

Monocytes were examined from ICA+ humans with a high risk of developing IDD, individuals with established SLE and autoimmune thyroid disease, and healthy controls. A portion of the pre-diabetic ICA+ individuals examined are enrolled in an IDD trial where they receive daily subcutaneous insulin as a preventative therapy. Monocytes of humans without autoimmune disease infrequently express PGS-2 mRNA ( 12%), whereas monocytes from subjects who are at high risk for the development of IDD express PGS-2 at a highly significant frequency(84%, p<0.0001). The preventative insulin therapy does not appear to affect PGS-2 mRNA or protein expression (see Table 2).

TABLE 2

PGS-2 mRNA expression in MOs of healthy controls and ICA+ subjects

|  | N | PGS-2 + | % Positive |
|---|---|---|---|
| Healthy controls | 25 | 3 | 12% |
| Females | 12 | 0 | 0% |
| Males | 13 | 3 | 23% |
| ICA+ | 31 | 26 | 84%* |
| Females | 17 | 12 | 80% |
| Males | 14 | 11 | 85% |
| Insulin RX | 14 | 10 | 71% |
| No RX | 17 | 16 | 94% |

Significant difference (p < 0.0001) analyzed by a two-tailed Fisher Test.

PGS-2 expression, however, is not specific for IDD, as humans with SLE and autoimmune thyroid disease also spontaneously express PGS-2 in their monocytes (see Table 3).

TABLE 3

PGS-2 expression in MOs of autoimmune controls

|  | N | PGS-2 + | % Positive |
|---|---|---|---|
| SLE | 5 | 4 | 80% |
| Hashimoto's | 4 | 2 | 50% |

In addition to the expression of PGS-2, the production of PGE2 by monocytes from these same control and autoimmune individuals was examined. It was found that PGE2 production, as determined by specific ELISA, is significantly higher in ICA+individuals and in autoimmune controls than in control monocytes (p<0.0001) (see Table 4).

TABLE 4

PGE$_2$ production by MOs of healthy controls, ICA+, and SLE subjects

|  | N | PGE$_2$ pg/ml |
|---|---|---|
| Healthy controls | 18 | 789 +/− 243* |
| ICA+/PGS-2 (+) | 23 | 7705 +/− 1510* |
| ICA+/PGS-2 (−) | 5 | 288 +/− 211 |
| ICA+/PGS-2 + /Ins. RX | 10 | 5805 +/− 1544 |
| SLE/PGS-2 + | 4 | 15437 +/− 12900 |

*significant difference (p < 0.0001) as analyzed by two-tailed Fisher Test.

Finally, the production of PGE2 was completely blocked by the PGS-2-specific inhibitor NS-398 (see FIG. 1).

Example 5—Monocyte Production of TNFα and IL-1β

The expression of PGS-2 can be induced by several factors including cytokines produced by monocytes such as TNFα and IL-1β. To evaluate the possibility that monocytes of pre-IDD subjects produce large quantities of IL-1 and TNFα which induces PGS-2, the levels of these cytokines were measured in supernatants of monocytes cultured in vitro for 24 hours from pre-IDD and healthy controls. As summarized in the table below, it was found that the levels of both IL-1 and TNFα produced by monocytes were actually lower in the pre-IDD subjects than in the controls (see Table 5). The lower levels of these cytokines is consistent with the constitutive production of prostaglandins which suppress the production of both TNFα and IL-1β. A comparison of TNFα and IL-1β levels between insulin-treated and untreated pre-IDD yielded no significant differences between these two groups.

TABLE 5

|  | N | pg/ml |
|---|---|---|
| IL-1β: |  |  |
| Healthy controls | 13 | 1455 ± 585 |
| ICA+ pre-IDD | 13 | 1189 ± 325 |
| TNFα: |  |  |
| Healthy controls | 10 | 718 ± 345 |
| ICA+ pre-IDD | 14 | 282 ± 91 |

IL-10production by monocytes of pre-IDD and healthy controls were also examined. It was found that there was no significant difference in the levels of IL-10 produced by either resting or stimulated monocytes from pre-IDD or healthy controls.

These data demonstrate that PGS-2 expression is not secondary to high levels of IL-1β or TNFα production or the lack of IL-10 secretion by pre-IDD monocytes. These findings support the notion that PGS-2 expression in the pre-IDD monocyte is a primary defect.

Example 6—PGS-2 mRNA Expression

PGS-2 mRNA expression has been found to be stable in the pre-IDD subjects as five individuals examined on more than one occasion (usually 3–6 months from the previous observation) remain positive. Likewise, six control subjects negative for PGS-2 remain negative with similar follow-up testing (see Table 6).

TABLE 6

| Subject group | PGS-2+/Total | %PGS-2+ |
|---|---|---|
| Healthy controls | 2/23 | 8.6 |
| ICA+ pre-IDD (observation) | 14/16 | 87.5* |
| ICA+ pre-IDD (insulin-treated) | 15/19 | 73.6** |
| ICA negative insulin autoantibody positive | 2/5 | 40 |
| ICA negative established IDD (>5 years) | 6/7 | 85.7*** |
| Systemic lupus erythematosus | 5/7 | 71**** |
| Autoimmune thyroiditis | 2/3 | 66 |

*vs. controls p = 0.0024 (unpaired Fisher's T test)
**vs. controls p = 0.0032
***vs. controls p = 0.025
****vs. controls p = 0.011

Example 7—PGS-2 Expression as Primary or Secondary Defect

Six long-term IDD patients (diabetes onset >5 years) and found that 5/6 of these individuals express PGS-2 have been analyzed. Studies show that ICA is lost in IDD patients within five years of the onset of clinical diabetes, reflecting a "burned out" autoimmune process. These data lend further support to the notion that PGS-2 is a primary monocyte defect in human IDD as it is in the NOD mouse.

Identification of PGS-2 as a primary defect enables the use of PGS-2 as an early cellular marker for IDD susceptibility. Differences in the PGS-2 gene of normal individuals and autoimmune subjects can be used to perform genetic screening of individuals to assess susceptibility to diabetes or other autoimmune disease.

Regardless of its status as a primary defect, PGS-2 expression reflects an active autoimmune process, and is highly advantageous in identifying individuals at high risk for IDD. In this regard, PGS-2-positive individuals who produce the highest levels of PGS-2 have progressed to clinical diabetes the fastest. It is also known that autoimmune diseases progress into spontaneous remissions or exacerbations. PGS-2 expression can be used to identify and/or monitor such changes in disease activity, i.e., PGS-2 positivity reflecting higher levels of disease activity and loss of PGS-2 expression reflecting remission. This is of great importance in IDD, where no physical signs or symptoms manifest to suggest exacerbation of the autoimmune attack on the insulin-producing cells.

PGS-2 is expressed in a high percentage of monocytes from individuals with autoimmune disorders such as SLE and thyroiditis. Thus, PGS-2 expression in monocytes can be employed as a cellular marker for other autoimmune diseases in addition to IDD. Of note in screening healthy controls is one individual whose monocytes were strongly positive for PGS-2 expression, who had no personal or family history of autoimmune diseases. This individual, six weeks post-screening, developed Raynaud's phenomenon and a strongly positive ANA, suggesting the development of a collagen vascular disease. This further supports the utility of the subject invention for general screening for autoimmune dysfunction.

Example 8—FACS Assay for PGS-2

One aspect of the invention is a fluorescent activated cell sorter (FACS) based assay for PGS-2 protein. Using this assay, it is possible to quantitate the percentage of cells in the peripheral blood that express the PGS-2 protein. This assay employs an antibody that specifically binds to the PGS-2 protein. The binding of this antibody to PGS-2 can be detected because the antibody is coupled to a fluorescent molecule which can be detected by the lasers of the FACS machine. Using this procedure, which requires only one-half teaspoon of blood, it is possible to detect the expression of PGS-2 protein in blood cells and determine the percentage of monocytes of pre-IDD individuals that constitutively express this enzyme.

Example 9—Uses, Formulations, and Administrations

Application of the treatments of the subject invention can be accomplished by any suitable method and technique presently or prospectively known to those skilled in the art.

In one embodiment, compounds of the subject invention have effective immunomodulatory activity. Specifically, they are useful in regulating immune responses in animals and humans. Thus, pharmaceutical compositions containing compounds of the invention as active ingredients are useful in prophylactic or therapeutic treatment of an immunomodulatory response in humans or other mammals.

The dosage administered will be dependent upon the immunomodulatory response desired; the type of host involved; its age, health, weight, kind of concurrent treatment, if any; frequency of treatment; therapeutic ration and like considerations.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising an active ingredient and one or more non-toxic, pharmaceutically acceptable carrier or diluent.

The compositions of the invention are advantageously used in a variety of forms, e.g., tablets, capsules, pills, powders, aerosols, granules, and oral solutions or suspensions and the like containing suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for inhibiting the development of insulin dependent diabetes wherein said method comprises administration to an individual in need of said treatment, a prostaglandin inhibitor in sufficient amount and duration to increase CD25 expression in said individual, wherein said prostaglandin inhibitor is not IL-10.

2. The method, according to claim 1, wherein said prostaglandin inhibitor is an inhibitor of PGS-2.

3. The method, according to claim 1, which further comprises the administration of an antigen.

4. The method, according to claim 3, wherein said antigen is an autoantigen.

* * * * *

UNITED STATES PATENT AND TRADEMARK OFFICE
CERTIFICATE OF CORRECTION

PATENT NO. : 6,168,792
DATED : January 2, 2001
INVENTOR(S) : Michael Clare-Salzer It is certified that error appears in the above-identified patent and that said Letters Patent is hereby corrected as shown below:

Column 2,
Line 47: "disease,: that" should read --disease, that--.

Column 4,
Line 3: "deject" should read --defect--.

Column 4,
Line 29: T cells" should read --T-cells--.

Column 5,
Line 9: "PGE2" should read --$PGE_2$--..

Column 5,
Line 43: IL4" should read --IL-4--.

Column 7,
Line 35: "individual;" should read --individual--.

Column 8,
Line 21: "PGE" should read --$PGE_2$--.

Column 11,
Line 29 (Table 2 footnote):"Significant" should read -- *Significant--.

UNITED STATES PATENT AND TRADEMARK OFFICE
CERTIFICATE OF CORRECTION

PATENT NO. : 6,168,792
DATED : January 2, 2001
INVENTOR(S) : Michael Clare-Salzer It is certified that error appears in the above-identified patent and that said Letters Patent is hereby corrected as shown below:

Column 12,
Line 27: "IL-10production" should read --IL-10 production--.

Column 12,
Line 54 (Table 6): "$71^{**}$" should read 71**--.

Signed and Sealed this

Twelfth Day of June, 2001

*Attest:*

*Attesting Officer*

NICHOLAS P. GODICI
*Acting Director of the United States Patent and Trademark Office*